(12) United States Patent
Cao

(10) Patent No.: US 8,068,916 B2
(45) Date of Patent: Nov. 29, 2011

(54) PURE DIGITAL MEDICAL AMPLIFIER FOR DIGITALLY ACQUIRING, CONDITIONING, STORING, AND TRANSFERRING CLINICAL AND NON-CLINICAL BIOMEDICAL SIGNALS

(75) Inventor: Yang Cao, Guangdong Province (CN)

(73) Assignee: Dimetek Digital Medical Technologies, Ltd., Shenzhen Guangdong Province (CN)

( * ) Notice: Subject to any disclaimer, the term of this patent is extended or adjusted under 35 U.S.C. 154(b) by 680 days.

(21) Appl. No.: 12/048,221

(22) Filed: Mar. 14, 2008

(65) Prior Publication Data
US 2009/0018458 A1 Jan. 15, 2009

(30) Foreign Application Priority Data
Jul. 13, 2007 (CN) .......................... 2007 1 0075885

(51) Int. Cl.
*A61N 1/08* (2006.01)
(52) U.S. Cl. ......................................................... 607/59
(58) Field of Classification Search .................... 607/30, 607/59, 60; 600/509, 544
See application file for complete search history.

(56) References Cited

U.S. PATENT DOCUMENTS
4,870,974 A * 10/1989 Wang ............................ 600/513
5,331,966 A * 7/1994 Bennett et al. ................ 600/508
2002/0068874 A1 * 6/2002 Zuckerwar et al. ........... 600/511
2002/0133087 A1 * 9/2002 Bayer et al. ................... 600/515
2006/0122529 A1 * 6/2006 Tsau ............................. 600/544

* cited by examiner

*Primary Examiner* — Niketa Patel
*Assistant Examiner* — Hiba El-Kaissi
(74) *Attorney, Agent, or Firm* — Morris Manning & Martin LLP; Tim Tingkang Xia, Esq.

(57) ABSTRACT

A new apparatus of pure digital medical amplifier used for clinical and non-clinical biomedical signal acquisition purposes is disclosed, which include: multiple single-stage amplification buffers connected to biomedical signal inputs for receiving and buffering various biomedical and reference signals, one or more high resolution analog-to-digital converter whose analog inputs connected to the output of said buffers for digitizing biomedical signals, one or more digital signal controller whose inputs/outputs are connected to said buffers and analog-to-digital converters for receiving the digitized biomedical signal data and controlling the processing and output of said digitized biomedical signal data according to preset control program or user's commands. By real-time or non-real-time method said digital signal controller does the following signal processing on the digitized biomedical signal data: filtering, compressing, decompressing, encoding, decoding, transferring, storing and retrieving, analyzing, and displaying the required said digitized biomedical signal data. This invention of amplifier requires only a few electronic components, and yields extremely low internal noise, extremely low distortion of analog output, extremely high external noise rejection and immunity, extremely high flexibility in filtering frequency setting for various biomedical signals.

8 Claims, 3 Drawing Sheets

PURE DIGITAL MEDICAL AMPLIFIER FOR DIGITALLY ACQUIRING, CONDITIONING, STORING, AND TRANSFERRING CLINICAL AND NON-CLINICAL BIOMEDICAL SIGNALS

BACKGROUND OF THE INVENTION

This invention relates to portable high performance medical amplifier, in particular to a pure digital medical amplifier for digitally acquiring, conditioning, storing, and transferring clinically and non-clinically applied biomedical signals.

Clinically and non-clinically applied biomedical signals, such as blood pressure, pulse, heartbeat, EEG, ECG, EMG, ERG, EOG, EGG, EP, ERP, AP, membrane potentials, ion potentials, ion currents, fluorescent currents, and optical electrical currents, are characterized by their low amplitude, and low frequency and near direct current signal components, usually below 30,000 Hz with major components in a range of 0.1-100 Hz.

The biomedical amplifiers been used widely both clinically and non-clinically nowadays are typically composed of the following stages: input buffer stage, pre-amplification stage, isolation amplification stage, high-pass filtering stage, low-pass filtering stage, notch filtering stage, post-amplification/attenuation stage, and output stage. The amplification gain is generally in the range from 1000 to 500000. The output amplitude is generally +/−0.1 to +/−10.0 volts, in order to meet the requirements such as display, measurement, recording, and acquisition of biomedical signals.

Such biomedical analog amplifiers described above have the following problems:

High internal noise, high signal distortion, and small dynamic range are the most serious problems. Multiple stages of amplification and filtering tend to generate much more internal noise than fewer stages because each stage contributes extra internal noise, and more peripheral electronic components also contribute more internal noise. Furthermore, multiple stages tend to consume more electric power and also add extra thermal noise. In addition, multiple stages need more circuit board space, the analog signal wires tend to be longer, and so are easier to introduce random noise as well as 50/60 Hz interference noise. Therefore, even a well designed analog medical amplifier typically suffers from internal noise level at 5-50 uV (RMS) or higher. As each stage causes analog signal distortion, an amplifier with multiple stages has significant signal distortion. When the amplification gain gets higher, the dynamic range of the amplifier becomes smaller. Commonly, the dynamic range of a biomedical amplifier with gain of 1000 is less than 10 mV, and that with gain of 500000 is less than 50 uV.

The filtering parameters are not changeable. The electronic filtering parameters are determined by the electronic components in the circuit, and cannot be changed once the amplifier is produced. For example, a notch filtering circuit designed for 50 Hz is not useable in the 60 Hz environment. The high-pass and low-pass filters are fixed once the amplifier design is over. This limits the versatile use of the amplifier for various applications, and the circuit must be specially designed in order to meet various filtering purposes.

There is no capability of signal processing and data analysis in these biomedical analog amplifiers. Analog signals can barely be processed and analyzed, and these signals need to be digitized before advanced processing and analysis can take place. The digitized biomedical signals often need various computations of signal processing and data analysis in real-time or non-real-time, such as low-pass filtering, high-pass filtering, notch filtering, data binning/insertion, data compression/decompression, data modulation/demodulation, time domain analysis, frequency domain analysis, waveform recognition, image processing, and result sorting. These computations require high performance digital signal controller in order to complete the tasks within few milliseconds. Currently various biomedical amplifiers are not capable of performing signal processing and data analysis.

The analog output from these biomedical analog amplifiers tends to worsen the signal quality, especially when output connection wire is long in distance and when connected device is contaminated with interference noise. High noise level, high distortion, small dynamic range, DC drifting, low efficiency, and high power consumption are typical in these amplifiers. To avoid interference noise introduced by a connected analog device, a linear photo isolator is often used, which further exacerbates the signal quality. Another approach been widely used to isolate the interference source is to modulate or digitize the biomedical signal, transfer the data via a digital photo isolator, and then demodulate or convert the data back to analog format for the next device. Unfortunately, this method suffers the same problems as these biomedical analog amplifiers with the cost of complicating the design and manufacturing.

The transferring efficiency is low for multiple channel biomedical signals. These analog amplifiers always use multiple connection wires for analog biomedical signal transferring. There is always signal cross talk between the parallel channels at certain degree, especially when the connection wire line is long. Furthermore, there is no way of compression for analog signals, and so the utilization of the signal transfer bandwidth is of low efficiency.

The signal transfer distance is limited. As the output of these analog amplifiers is in analog format, the signal quality degrades quickly with the transfer distance. If wireless approach is applied for long distance signal transfer, the analog signals must be modulated and then demodulated in order to achieve the signal transfer, and the signal quality will be affected. Currently only digitized signals can be transferred remotely with high fidelity and no loss.

The signals have poor security during transfer. Clinically applied biomedical signals may involve patient's sensitive information, and should be secured in general. However, analog signals are not easily encrypted and so cannot be effectively secured. This results in that the analog signals from analog biomedical amplifiers may be captured and abused during remote transfer, especially radio frequency transfer as the radio signal is aimlessly scattered in the space.

BRIEF SUMMARY OF THE INVENTION

This invention is aimed to providing a pure digital medical amplifier for clinical and non-clinical biomedical signals to solve the problems of the existing analog multi-stage biomedical amplifiers. A new design methodology is now disclosed where design is composed of the following:

Multiple single-stage amplification buffers that are connected to high impedance biomedical and reference signal sources;

one or more high resolution analog to digital convertor (ADC), wherein the inputs are connected to the outputs of said multiple single-stage amplification buffers;

a digital signal controller (DSC) that controls said ADC and receives digitized biomedical signal data via the connection of its input port and outputs of ADC, and performs information processing and data output, according to the preset control program or user's commands.

A prior scheme of said DSC used in said pure digital medical amplifier includes:

a channel selection control unit for selecting one or multiple channels of analog biomedical signal inputs;

a data acquisition control unit connected to said channel selection control unit and ADC for digitizing and acquiring biomedical signal data;

a memory unit connected to said data acquisition control unit for storing the acquired and digitized biomedical signal data;

an information processing unit connected to said memory unit for processing and analyzing said digitized biomedical signal data.

A prior scheme of processing method of said information processing unit in said DSC include:

real-time digital signal filtering, wherein said digitized biomedical signal data is filtered within 50 msec after it is acquired; or non-real-time filtering, wherein said digitized biomedical signal data is stored in said memory unit for later filtering any time after the data is acquired;

real-time data processing, wherein said digitized biomedical signal data is processed within 50 msec after it is acquired; or non-real-time data processing, wherein said digitized biomedical signal data is stored in said memory unit for later data processing any time after the data is acquired;

real-time data analysis, wherein said digitized biomedical signal data is analyzed within 50 msec after it is acquired; or non-real-time data analysis, wherein said digitized biomedical signal data is stored in said memory unit for later data analysis any time after the data is acquired;

real-time data modulation and output, wherein said digitized biomedical signal data is modulated and outputted within 50 msec after it is acquired; or non-real-time data modulation and output, wherein said digitized biomedical signal data is stored in said memory unit for later data modulation and output any time after the data is acquired.

A prior scheme of said information processing unit includes one or more of following modules:

a digital filtering module connected to said memory unit, wherein said digitized biomedical signal data is digitally filtered by low-pass filter, high-pass filter, band-pass filter, and or notch filter;

a data processing module connected to said memory unit, wherein said digitized biomedical signal data is processed by algorithms including binning and insertion, compression and decompression, encryption and decryption, and or modulation and demodulation;

a data analysis module connected to said memory unit, wherein said digitized biomedical signal data is analyzed by algorithms including time-domain analysis, frequency-domain analysis, waveform recognition, and or image analysis;

a data modulation and output module connected to said memory unit, wherein said digitized biomedical signal data is used to modulate the pulse width of the pulse train output.

A prior scheme of this invention of pure digital medical amplifier for clinical and non-clinical biomedical signals also includes full differential direct current amplification buffers for impedance conversion and low gain amplification.

A prior scheme of this invention of pure digital medical amplifier for clinical and non-clinical biomedical signals also includes:

a data modulation output module, wherein its inputs are connected to said DSC PWM output ports;

a wireless communication modules, wherein its inputs are connected to said DSC UART or SPI output ports for remote biomedical signal data transfer;

serial communication modules, such as SPI, UART, I2C, USB, and Ethernet, wherein the inputs are connected to said DSC I/O ports for transferring said digitized and processed biomedical signal data to other relevant devices;

a parallel communication module, wherein its inputs are connected to said DSC parallel port.

A prior scheme of said data modulation output module is composed of electrical isolation digital drivers such as photo-coupler, magnetic-coupler, capacitor-coupler, fiber-optics-transceiver, light-emission-diode-transceiver, radio-frequency-transceiver, and wireless communication transceiver, or direct wire connection.

A prior scheme of width modulated pulse trains is that said DSC sets pulse trains to its PWM port, and modulates the pulse width with the amplitude of said digitized and processed biomedical signal data, whereby the PWM port sends the corresponded biomedical signals in analog format by a simple low-pass filtering.

A prior scheme of the output port of data modulation output module is connected to analog devices for direct analog biomedical signal recording and display.

A prior scheme of data transfer is that said DSC transfers the digitized biomedical signal data with information processing of digitally filtering, and/or data processing, and/or data analysis, to other remote relevant devices via wired or wireless communication methods with said modules such as serial communication module, parallel communication module, and wireless communication module.

This invention also discloses a new pure digital medical amplifier for clinical and non-clinical biomedical signals, including:

analog-to-digital converters, wherein said biomedical signal sources are connected to the inputs;

a digital signal controller, wherein it receives the outputs of said analog-to-digital converters, and controls the acquisition, information processing, and output of said digitized biomedical signal data, according to preset control program or user's commands.

A prior scheme of this invention of pure digital medical amplifier for clinically and non-clinically applied biomedical signals also includes: multiple full differential amplification buffers whose inputs are connected to said biomedical signal sources and outputs are connected directly to said analog-to-digital converters for impedance conversion and direct current low gain amplification.

The disclosed apparatus and methodology of said pure digital medical amplifier features a circuit with few analog electronic components, and so the internal noise generated by electronic devices is minimized; this also greatly enhances the immunity to power line frequency interference. Furthermore, other analog devices do not introduce any extra noise as the amplifier's analog output is of digital format and isolated by digital driver.

The use of digital filtering makes this invention of pure digital medical amplifier flexible for setting up any combination of low-pass, high-pass, and notch filter frequencies to meet various requirements of frequency range from 0 to 30 kHz for different biomedical signal recordings. It is of high accuracy and stability, and is of very low noise because of digital filtering feature and void using analog filtering electronic components.

The outputs of this invention are pure digital, including that to the analog devices, and are capable of transferring the biomedical signal data of multiple channels via a single port. With lossless compression, the data transfer efficiency is greatly enhanced, so that large amount of data from multiple channels or at a high sample rate can be transferred in real time at relatively low bandwidth data communication methods, as well as the power consumption for transferring biomedical signal data is greatly reduced due to shorter transfer time. The encryption of patient's sensitive information during data transfer is helpful for patient information security.

The data transfer of this invention is either via wire connection, or wireless communication modules such as Bluetooth module, Wi-Fi module, and GPRS/CDMA/WCDMA module, which enhance the transfer distance and eliminate the distance limitation of wire connection.

The isolation digital drivers for pulse width modulation output makes said pure digital medical amplifier output not only digitized and processed biomedical signal data, but also the waveforms compatible to those traditional analog biomedical devices with digital signal processing advantages. The output can be connected directly to various traditional display and recording devices such as audio monitor, oscilloscope, tape recorder, plotter, etc. As the methodology of pulse width modulation is used, this type of analog output has many merits such as high fidelity, high efficiency, high noise rejection, high overloading, and very low output impedance.

This invention has very high power line interference rejection capability, much better than the traditional analog amplifiers, and can be used for microvolt signal recording in electrically complicated environments such as operating rooms and ICU rooms, and needs no special grounding.

Because of its superior external noise rejection and extremely low internal noise level, this invention of pure digital medical amplifier not only can be used in recording conventional biomedical signals in various frequency ranges, but also makes it possible for some biomedical signals not available for current analog amplifiers.

This invention of pure digital medical amplifier can be widely used not only for extremely difficult and small biomedical signal recordings, but also for patient tele-recording, tele-diagnosis, and tele-monitoring, as its analog circuitry is simple, few electronic components are used, powerful real-time information processing are implemented, data transfer is highly efficient, data being transferred is secured, and the amplifier device is small, light, and power saving.

DETAILED DESCRIPTION OF THE INVENTION

This invention of pure digital medical amplifier is further described by specific implementation methods as follows.

Figure 1:
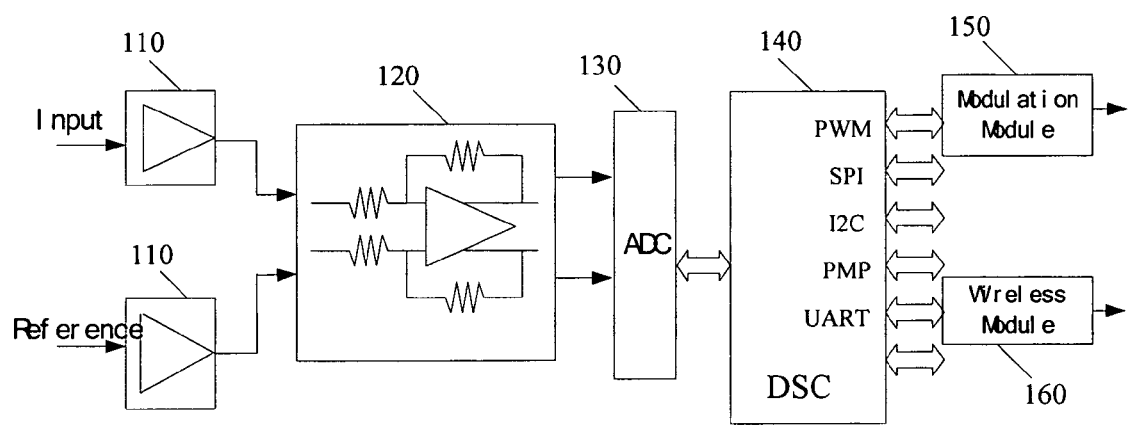
FIG. 1 is a diagram showing the structural block of this invention of pure digital medical amplifier.

As shown in FIG. 1, this invention of pure digital medical amplifier is composed of high impedance input amplification buffer (110), full differential amplifier (120), high resolution ADC (130), DSC (140), isolation digital PWM driver module (150), and wireless communication module (160).

Figure 2A:
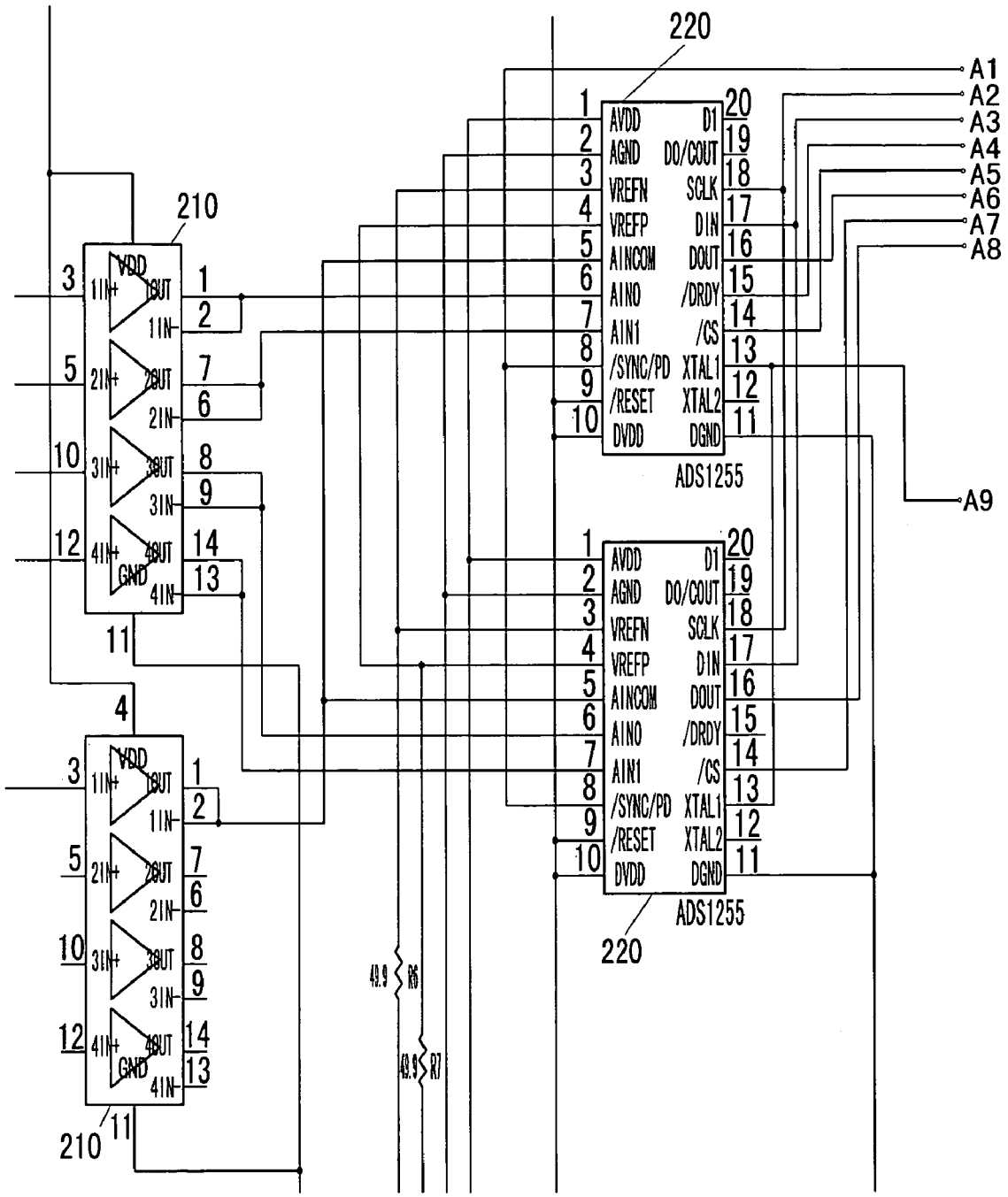
FIGS. 2A and 2B are a diagram showing a prior example of the circuitry.
Figure 2B:
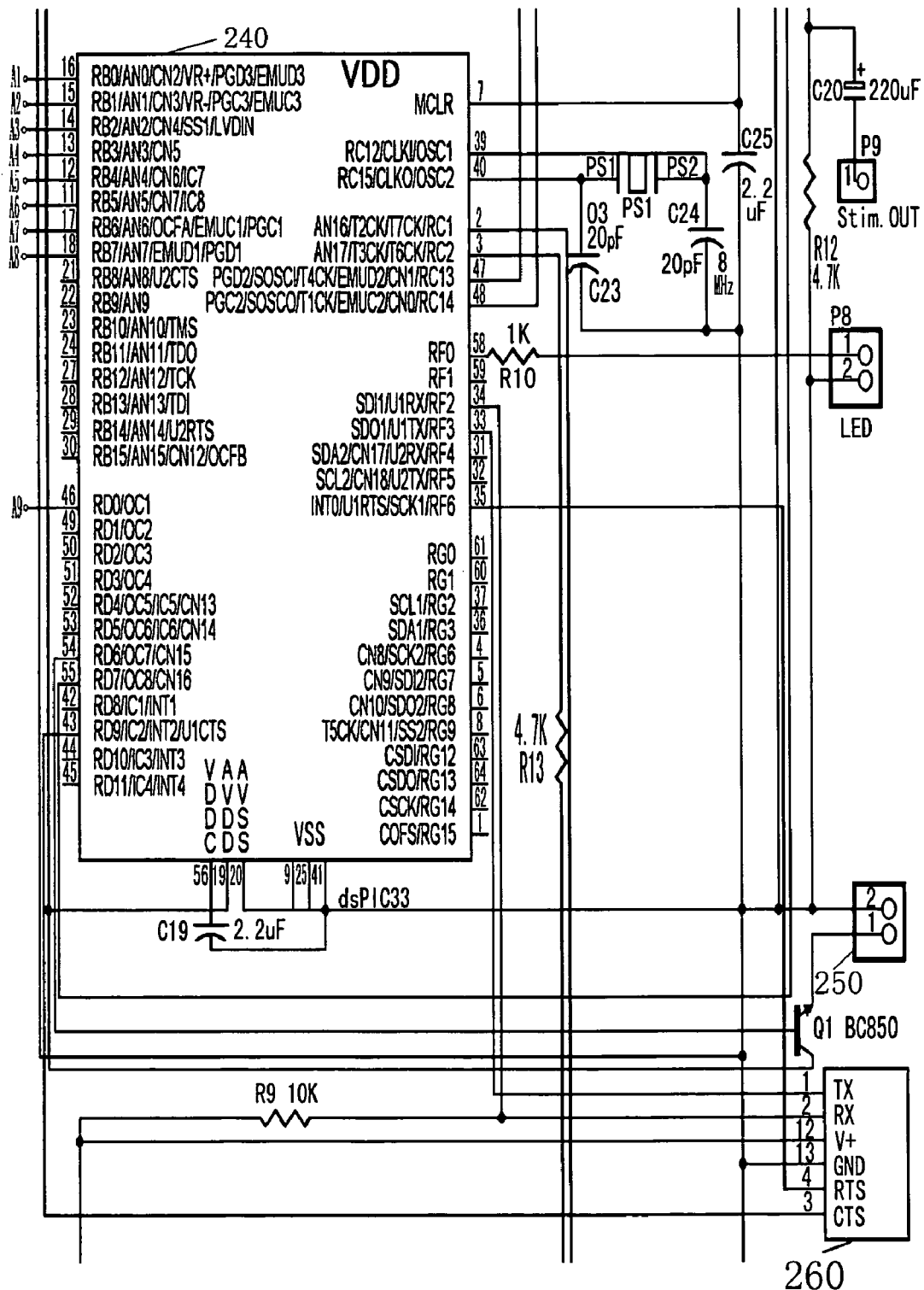

Also as shown in FIG. 2, the high impedance input amplification buffer is composed of multiple low noise operation amplifiers (210). For example, the low noise operation amplifiers 210 can be realized by using IC model named TLC274. The number of use of operation amplifiers is dependent on the number of total biomedical signal inputs plus reference input, for example there will be 5 said low noise operation amplifier 210 when the total biomedical signal inputs are 5. The positive input of each operation amplifier receives biomedical signal input, and the negative input is connected to its output, in order to enhance the input impedance to 10-1000 mega ohms or higher.

It should be mentioned that said the high impedance input amplification buffer is used for meeting the high impedance nature of most biomedical signal sources. The buffers can be omitted when low impedance biomedical signals are inputted.

In addition, the outputs of said low noise operation amplifiers 210 are connected to the inputs of said full differential amplifier 120. Said full differential amplifier amplifies the biomedical signals in the frequency range from 0 to 30 kHz. In general, the gain is set to about 10-100; while for some biomedical signals with amplitude above 1 millivolt, the gain can be set to 1; in other words, said full differential amplifier 120 can be omitted for large amplitude biomedical signals. The full differential amplifier 120 can also omitted for relative large biomedical signals by setting said low noise operation amplifiers 210 to gain of 1.

The outputs of said full differential amplifier 120 are connected to the input ports of said high resolution ADC 130 with resolution of 16 bits or above. The conversion rate is designed to be 200 sps and above, up to 120 ksps or even higher.

In addition, the model selection of said ADC 130 is based mainly on the number of input channels and the frequency requirement for the biomedical signals. For example, if the number of input channels is 1-4, and the frequency requirement is below 30 kHz, ADS1255, ADS1256, and ADS1274 can be selected; if the number of input channels is 16-32, or the frequency requirement is above 30 kHz, ADS1258 and ADS1278 can be selected; if the amplitude of biomedical signals is above 50 uV, 16 bits ADC such as ADS8341 can be selected.

It should be mentioned that some ADC chips also contain amplification circuitry (such as ADS1255, ADS1256), and so the full differential amplifier 120 can also utilize the internal amplification circuitry. That is, the full differential amplifier 120 in FIG. 1 and ADC can be integrated in one chip; for example, said full differential amplifier 120 and said ADC 130 can be integrated in one chip as shown ADC circuitry 220 in FIG. 2.

The digital outputs of said ADC 130 are connected to the high performance DSC 140. Said DSC 140 can be either 16 bits (such as dsPIC33 series) or 32 bits (such as PIC32 series and TMS320 series); both types of DSC have the consistent circuitry with different internal architecture, wherein the 16 bits DSCs have lower MIPS speed and power consumption mainly for portable and power saving purposes, while the 32 bits DSCs have higher MIPS speed and power consumption mainly for more computational purposes.

The pulse width modulation (PWM) ports of DSC 140 are connected to the module of isolation digital drivers 150, which can be of photo-coupler (e.g. PS9113), magnetic-coupler (e.g. IL260), capacitor-coupler (e.g. ISO721), fiber-optics transceiver (e.g. APTX179), or light emission diode (LED). The outputs of module 150 are used for electrically isolated analog outputs of the processed biomedical signals. Practically, the module 150 can be omitted when there is no interference noise from the connected analog devices to said pure digital medical amplifier.

In addition, the universal asynchronous receiver/transmitter (UART) port said DSC 140 is connected to said wireless communication module 160. Such a connection can also be made via serial peripheral interface (SPI), in order to transfer commands and data between said pure digital medical amplifier and other computerized devices.

In addition, the IC 240 in FIG. 2 corresponds to DSC 140 in FIG. 1; components 250 and 260 in FIG. 2 correspond to modulation output module 150 and wireless communication module 160 in FIG. 1.

The working principles of this invention of pure digital medical amplifier are summarized as follows:

Said DSC 140 receives commands from the predefined program or data transfer ports such as a UART port to receive user's control commands in order to control analog to digital conversion, data acquisition, and information processing. The biomedical signal input can be of either single channel or multiple channels, where the channels activated are determined by commands from DSC 140. As the data acquisition starts, DSC 140 sends data acquisition related commands to the channel selection module via data I/O control ports to accomplish high resolution analog to digital conversion; said DSC 140 acquires digitized biomedical signal data and stores in the connected random access memory (RAM).

When desired data sample rate is lower than the channel highest sample rate (i.d. a slower sample rate), each sample data acquired according to the channel selection superimposes to the corresponded channel data and are stored in RAM, where the channel lag time is calculated as:

$$T = \text{ADC time } T1 + \text{conversion time } T2$$

For example, if total channel number is N and the superimposition number is M, the multiple channel sample rate $SPS = 1/(T*N*M)$.

Said DSC 140 performs said information processing algorithms and stores the results in the RAM according to the predefined program or control commands. The information processing algorithms include but not limited to low-pass filtering, high-pass filtering, band-pass filtering, notch filtering, data binning and insertion, data compression and decompression, data encryption and decryption, data modulation and demodulation, time domain analysis, frequency domain analysis, waveform recognition, image processing, result judgments, etc.

In addition, said DSC 140 operates real-time filtering on the digitized biomedical signal data stored in the RAM, and stores the filtered data back into the RAM, or transfers to corresponded ports and modules (such as the serial port, parallel port, USB module, wireless communication module, PWM module, etc.), wherein the procedure of data acquisition is not affected by said filtering operation. Said DSC 140 also operates non-real-time filtering on the digitized biomedical signal data stored in the RAM, and stores the filtered data back into the RAM, or transfers to corresponded ports and modules, wherein the filtering operation is dependent on the dimension of the data array, which is limited by the RAM space.

Said DSC 140 also transfers digitized and processed biomedical signal data stored in the RAM to other devices. Said biomedical signal data can be compressed by said DSC 140 and so the data transfer rate is greatly enhanced, wherein the algorithms include but not limited to Huffman, ACE, ARC, ARJ, CAB, LZ, LZH, LZW, GZIP, ZIP, 7-ZIP, RAR, and so on. For instance, a sixteen channel biomedical signal data acquired at 200 samples per second yields data generation rate at 200×16×4=12800 bytes per second, which is compressed to less than 2000 bytes per second and becomes continuously transferable through 20 kbps bandwidth communication network. In less frequent application, the same scheme can be used for continuously transferring data of two channels at 1600 samples per second data generation rate.

Said DSC 140 can also start outputting said biomedical signal data by using a PWM port, where the width of pulse trains at 10000 cycles per second or higher is modulated by the amplitude of said biomedical signal. The port yields high fidelity analog waveform output via a simple low pass filtering circuit, even for very low frequency (<0.5 Hz) signal components.

In summary, this invention of pure digital medical amplifier has the following technical significances:

1. The disclosed apparatus and methodology of said pure digital medical amplifier features a circuit with few analog electronic components, and so the internal noise generated by electronic devices is minimized; this also greatly enhances the immunity to power line frequency interference. Furthermore, other analog devices do not introduce any extra noise as the amplifier's analog output is of digital format and isolated by digital driver.

2. The use of digital filtering makes this invention of pure digital medical amplifier flexible for setting up any combination of low-pass, high-pass, and notch filter frequencies to meet various requirements of frequency range from 0 to 30 kHz for different biomedical signal recordings. It is of high accuracy and stability, and is of very low noise because of digital filtering feature and void using analog filtering electronic components.

3. The outputs of this invention are pure digital, including that to the analog devices, and are capable of transferring the biomedical signal data of multiple channels via a single port. With lossless compression, the data transfer rate is greatly enhanced, so that large amount of data from multiple channels or high sample rate can be transferred in real time at relatively low bandwidth data communication methods, as well as the power consumption for transferring biomedical signal data is greatly reduced. The encryption of patient's sensitive information during data transfer is helpful for patient information security.

The data transfer of this invention is either via wire connection, or wireless communication modules such as Bluetooth module, Wi-Fi module, and GPRS/CDMA/WCDMA module, which enhance the transfer distance and eliminate the distance limitation of wire connection.

The isolation digital drivers for pulse width modulation output makes said pure digital medical amplifier output not only digitized and processed biomedical signal data, but also the waveforms compatible to those traditional analog biomedical devices with digital signal processing advantages. The output can be connected directly to various traditional display and recording devices such as audio monitor, oscilloscope, tape recorder, plotter, etc. As the methodology of pulse width modulation is used, this type of analog output has many merits such as high fidelity, high efficiency, high noise rejection, high overloading, and very low output impedance.

This invention has power very high line interference rejection capability, much better than the traditional analog amplifiers, and can be used for microvolt signal recording in electrically complicated environments such as operating rooms and ICU rooms, and needs no special grounding.

Because of its superior external noise rejection and extremely low internal noise level, this invention of pure digital medical amplifier not only can be used in recording conventional biomedical signals in various frequency ranges, but also makes it possible for some biomedical signals not available for current analog amplifiers.

This invention of pure digital medical amplifier can be widely used not only for extremely difficult and small biomedical signal recordings, but also for patient tele-recording, tele-diagnosis, and tele-monitoring, as its analog circuitry is simple, few electronic components are used, powerful real-time information processing are implemented, data transfer is highly efficient, data being transferred is secured, and the amplifier device is small, light, and power saving.

What is claimed is:

1. A pure digital medical amplifier comprising: multiple single-stage low gain amplification buffers for receiving and buffering various biomedical and reference signals, wherein each of the single-stage amplification buffers comprises: an input configured to receive biomedical signals, wherein the biomedical signals are one of clinical and non-clinical signals; and an output configured to output buffered biomedical signals; a high resolution analog-to-digital converter (ADC) comprising: analog inputs connected to the outputs of the amplification buffers and configured to receive the buffered biomedical signals data; an ADC component configured to perform analog to digital conversion by converting analog signals of the buffered biomedical signal data into digitized biomedical signal data; and digital outputs configured to output the digitized biomedical signal data; and control ports; and a high performance digital signal controller (DSC) comprising: at least one controller; a plurality of input ports and output ports; at least one digital signal processor, configured to receive, and process the digitized biomedical signal data from said ADC, wherein the input ports receive digitized biomedical signal data from the ADC, and the digitized biomedical signal data are configured to be filtered, conditioned, analyzed, and transferred by the digital signal processors according to a preset control program or commands received from communication ports; wherein one or more output ports of the output ports are configured to output control signals to the ADC and the multiple single-stage low gain amplifier according to the preset control program or the commands received from the communication ports, and one or more output ports of the output ports are configured to output the processed data according to the preset control program or the commands received from the communication ports to one or more modules.

2. The pure digital medical amplifier of claim 1, wherein said DSC includes: a channel selection control unit configured to select one or more biomedical signal input channels; a data acquisition control unit that is connected to said channel selection control unit and the control ports of said ADC for controlling the acquisition of the biomedical signal data; a memory unit for storing said digitized biomedical signal data; and an information processing unit configured to process said digitized biomedical signal data.

3. The pure digital medical amplifier of claim 2, wherein said information processing unit includes
at least one module selected from following modules: a digital signal filtering module that is connected to said memory unit and configured to perform digital low-pass filtering, digital high-pass filtering, digital notch filtering, for digitally conditioning said digitized biomedical signal data stored in said memory unit;
a data processing module that is connected to said memory unit and configured to perform data binning and insertion, compression and decompression, data modulation and demodulation, encryption and decryption, for further digitally processing said digitized biomedical signal data stored in said memory unit; a data analysis module that is connected to said memory unit and configured to perform time domain analysis, frequency domain analysis, pattern recognition, and image analysis, for analyzing said digitized biomedical signal data stored in said memory unit; and
a data modulation output module that is connected to said memory unit and configured to modulate the pulse width of pulse outputs with the amplitude of said biomedical signals for outputting said digitized biomedical signal data stored in said memory unit.

4. The pure digital medical amplifier of claim 3, wherein said information processing unit includes the following modules for performing information processing on said digitized biomedical signal data:
said digital signal filtering module configured to perform signal filtering immediately after said biomedical signal data has been acquired within a delay of 50 milliseconds by real-time method, or configured to perform signal filtering of said biomedical signal data stored in said memory unit any time after the data has been acquired by non-real-time method; said data processing module configured to perform data processing immediately after said biomedical signal data has been acquired within a delay of 50 milliseconds by real-time method, or configured to perform data processing of said biomedical signal data stored in said memory unit any time after the data has been acquired by non-real-time method; said data analysis module configured to perform data analysis immediately after said digitized biomedical signal data has been acquired within a delay of 50 milliseconds by real-time method, or configured to perform data analysis of said biomedical signal data stored in said memory unit any time after the data has been acquired by non-real-time method; and
said data modulation output module configured to perform said data modulation output immediately after said biomedical signal data has been acquired within a delay of 50 milliseconds by real-time method, or configured to perform data modulation output of said biomedical signal data stored in said memory unit any time after the data has been acquired by non-real-time method.

5. The pure digital medical amplifier of claim 1, wherein said single-stage amplification buffers are configured to use full differential direct current amplification at a gain lower than 100 without additional analog filtering.

6. The pure digital medical amplifier of claim 1, wherein the DSC is provided with a pulse width modulation (PWM) output, and a Universal Asynchronous Receiver Transmitter (UART), Serial Peripheral Interface (SPI), Inter-Integrated Circuit (I2C), Universal Serial Bus (USB) or Ethernet port, and a parallel communication port, and the DSC is configured to be connected to one or more electronic devices, and the pure digital medical amplifier further comprises:
a modulation output module which has an input, wherein the PWM output of said DSC is connected to the input of the modulation output module for transferring said digitized biomedical signal data configured to be processed by real-time or non-real-time method, and the modulation output module takes form of photo-isolation drivers, magnetic-isolation drivers, fiber-optics transceivers, light-emission diodes, or wire connection;
a radio-frequency communication module, wherein the Universal Asynchronous Receiver Transmitter (UART) or Serial Peripheral Interface (SPI) port of said DSC is connected to input/output port of the radio-frequency communication module for transferring wirelessly said digitized biomedical signal data configured to be processed by real-time or non-real-time method between said pure digital medical amplifier and the electronic devices; a serial communication module, wherein the SPI, UART, Inter-Integrated Circuit (I2C), Universal Serial Bus (USB), or Ethernet port of said DSC is configured to be connected to the electronic devices for transferring said digitized biomedical signal data processed by real-time or non-real-time method; and a parallel communication module, wherein the parallel communication port of said DSC is configured to be connected to the electronic device for transferring said digitized biomedical signal data configured to be processed by real-time or non-real-time method.

7. The pure digital medical amplifier of claim 6, wherein the PWM output of the DSC is configured to perform pulse width modulation of pulse output by the amplitude of said digitized biomedical signals configured to be processed by real-time or non-real-time method, therefore the PWM output yields analog signal of the corresponding digitized biomedical signal data; and output port of said data modulation output module is configured to connect analog devices which are configured to acquire, record, or display analog biomedical signals.

8. The pure digital medical amplifier of claim 3, wherein that further comprises a wireless communication module, a serial communication module, and or a parallel communication module; said digitized biomedical signal data filtered, processed, and or analyzed by said DSC is configured to be transferred remotely to other relevant electronic devices by the wireless communication module, serial communication module and or parallel communication module.

* * * * *